US007457963B2

(12) United States Patent
Ito et al.

(10) Patent No.: US 7,457,963 B2
(45) Date of Patent: Nov. 25, 2008

(54) ENDOSCOPIC EXAMINATION SYSTEM WITH SECURITY FOR REPORT PRESERVATION OR TRANSMISSION IMPROVED

(75) Inventors: Nobuyasu Ito, Hachioji (JP); Shinichi Omori, Hachioji (JP); Makoto Watai, Northport, NY (US); Asuka Kawamura, Hachioji (JP)

(73) Assignee: Olympus Corporation, Tokyo (JP)

( * ) Notice: Subject to any disclaimer, the term of this patent is extended or adjusted under 35 U.S.C. 154(b) by 815 days.

(21) Appl. No.: 10/202,140

(22) Filed: Jul. 24, 2002

(65) Prior Publication Data
US 2003/0018640 A1      Jan. 23, 2003

(30) Foreign Application Priority Data
Jul. 27, 2001    (JP)    ............................. 2001-228162

(51) Int. Cl.
G06F 21/20    (2006.01)
G06F 21/22    (2006.01)
G06F 21/24    (2006.01)
G06F 11/30    (2006.01)

(52) U.S. Cl. .................. 713/182; 713/183; 713/184; 713/185; 726/2; 726/3; 726/4; 726/16; 726/17

(58) Field of Classification Search .............. 713/166, 713/183
See application file for complete search history.

(56) References Cited

U.S. PATENT DOCUMENTS 5,740,801 A * 4/1998 Branson ................. 600/407
5,877,819 A * 3/1999 Branson ................. 348/701
6,819,785 B1 * 11/2004 Vining et al. ........... 382/128
6,990,492 B2 * 1/2006 Gupta ..................... 707/9
7,043,437 B1 * 5/2006 Nielsen et al. .......... 704/270.1
2001/0034617 A1 * 10/2001 Kimata .................... 705/3

FOREIGN PATENT DOCUMENTS

| EP | 0 267 259 B1 | 5/1988 |
|---|---|---|
| EP | 0 945 775 A2 | 9/1999 |
| EP | 0 316 911 A2 | 6/2003 |
| JP | 04-340160 | 11/1992 |
| JP | 10-177524 | 6/1998 |
| JP | 10-248805 | 9/1998 |
| JP | 10-272094 | 10/1998 |
| JP | 2001-112721 | 4/2001 |
| JP | 2001-175795 | 6/2001 |
| WO | WO 01/44990 | 6/2001 |

* cited by examiner

Primary Examiner—Syed A. Zia
(74) Attorney, Agent, or Firm—Scully, Scott, Murphy & Presser, P.C.

(57) ABSTRACT

An endoscopic examination system consists mainly of an examination terminal, a report input/output terminal, and a server. The examination terminal is connected to endoscopic examination equipment. The report input/output terminal is used to enter environmental information concerning the details of an environment under which an endoscopic examination is performed (an examining doctor's name, a name of equipment employed, etc.), and reporting information concerning the results of an endoscopic examination (findings, diagnosis, etc.). The examination data (endoscopic image data, etc.) sent from the examination terminal, and the reporting information and examination request sent from the report input/output terminal server are preserved in the server.

20 Claims, 13 Drawing Sheets

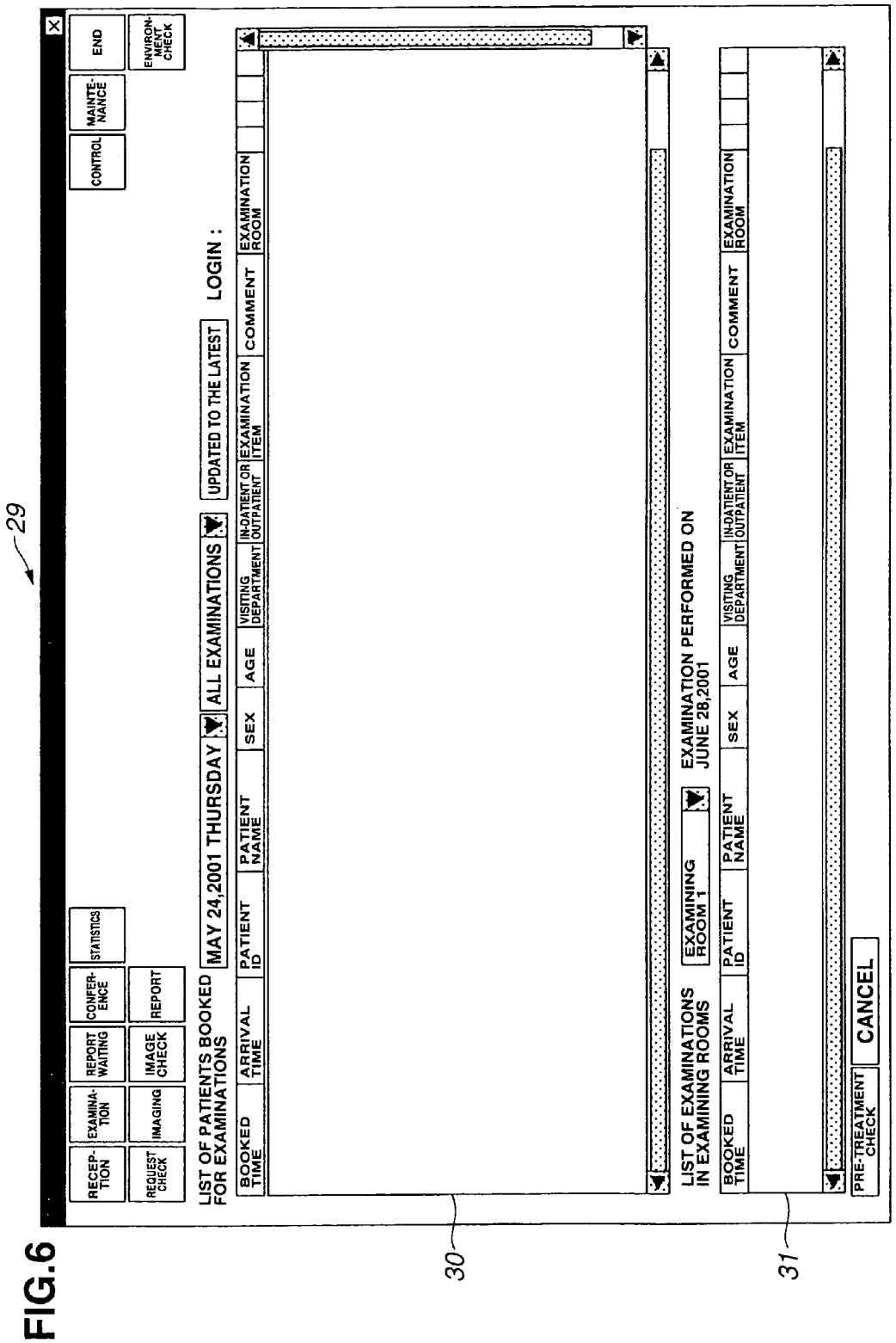

FIG.7

BASIC PATIENT DATA

ORDER

ENVIRONMENTAL INFORMATION
- DATE OF EXAMINATION: MAY 24, 2001, THURSDAY
- EXAMINED PERSON: TARO HACHIOJI
- RESPONSIBLE EXAMINING DOCTOR:
- ASSISTANT DOCTOR: TAKASHI HACHIOJI
- NURSE: HANAKO HACHIOJI | KAORI HACHIOJI
- ENDOSCOPE NUMBER:
- ROOM NUMBER:
- TIME OF EXAMINATION:

PRE-TREATMENT ITEM
NOTES
- ☐ XYLOCAINE SHOCK    ☐ BUSCOPAN SHOCK    ☐ PROSTATOMEGALY    ☐ CARDIAC DISEASE
- ☐ GLAUCOMA    ☐ DIABETES    ☐ 60 YEARS OLD OR MORE

| IN-PATIENT | OUT-PATIENT | ITEM | DEGREE | TIME OF TREATMENT | PLACE OF TREATMENT | TREATING PERSON |
|---|---|---|---|---|---|---|

EXAMINING DRUG

| CHEMICAL NAME | QUANTITY | TIME |
|---|---|---|

EQUIPMENT

| EQUIPMENT NAME | QUANTITY |
|---|---|

ACCOUNTING INFORMATION

TECHNIQUE

| TECHNIQUE NAME | NUMBER OF TIMES |
|---|---|

ADDITION

| ADDITION NAME | NUMBER OF TIMES |
|---|---|

PRINTING            COMPLETION | PENDING

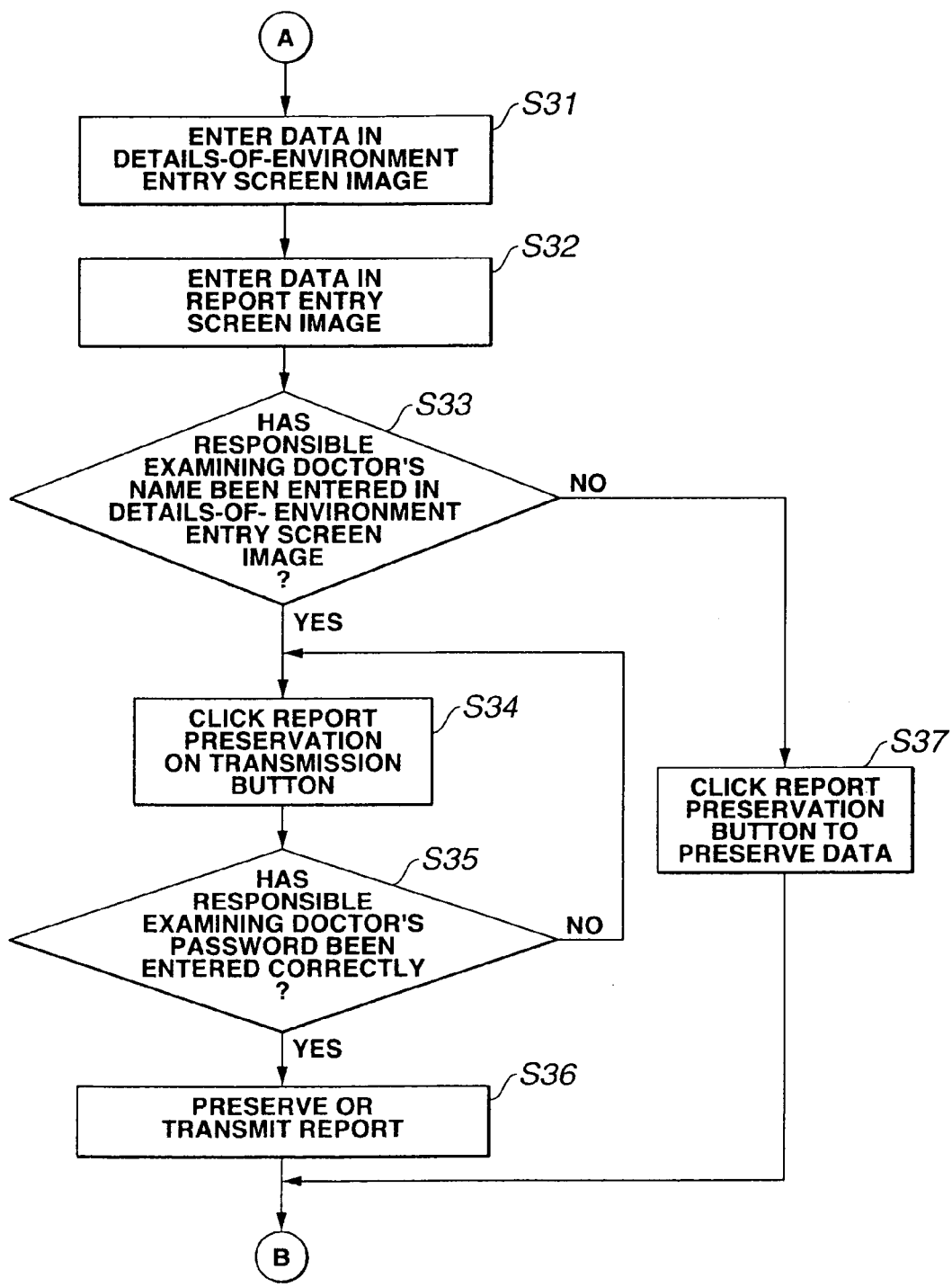

FIG.10

BASIC PATIENT DATA

ORDER

ENVIRONMENTAL INFORMATION

| DATE OF EXAMINATION | MAY 24, 2001, THURSDAY | TIME OF EXAMINATION |
|---|---|---|
| EXAMINED PERSON | TARO HACHIOJI | |
| RESPONSIBLE EXAMINING DOCTOR | TAKASHI HACHIOJI | |
| ASSITANT DOCTOR | | |
| NURSE | HANAKO HACHIOJI | KAORI HACHIOJI |
| ENDOSCOPE NUMBER | | |
| ROOM NUMBER | | |

PRE-TREATMENT ITEM

NOTES

☐ XYLOCAINE SHOCK ☐ BUSCOPAN SHOCK ☐ PROSTATOMEGALY ☐ CARDIAC DISEASE

☐ GLAUCOMA ☐ DIABETES ☐ 60 YEARS OLD OR MORE

| | ITEM | DEGREE | TIME OF TREATMENT | PLACE OF TREATMENT | TREATING PERSON |
|---|---|---|---|---|---|
| IN-PATIENT / OUT-PATIENT | | | | | |

ACCOUNTING INFORMATION

TECHNIQUE

| TECHNIQUE NAME | NUMBER OF TIMES |

ADDITION

| ADDITION NAME | NUMBER OF TIMES |

EXAMINING DRUG

CHEMICAL NAME | QUANTITY | TIME

EQUIPMENT

EQUIPMENT NAME | QUANTITY

PRINTING

COMPLETION | PENDING

FIG.11

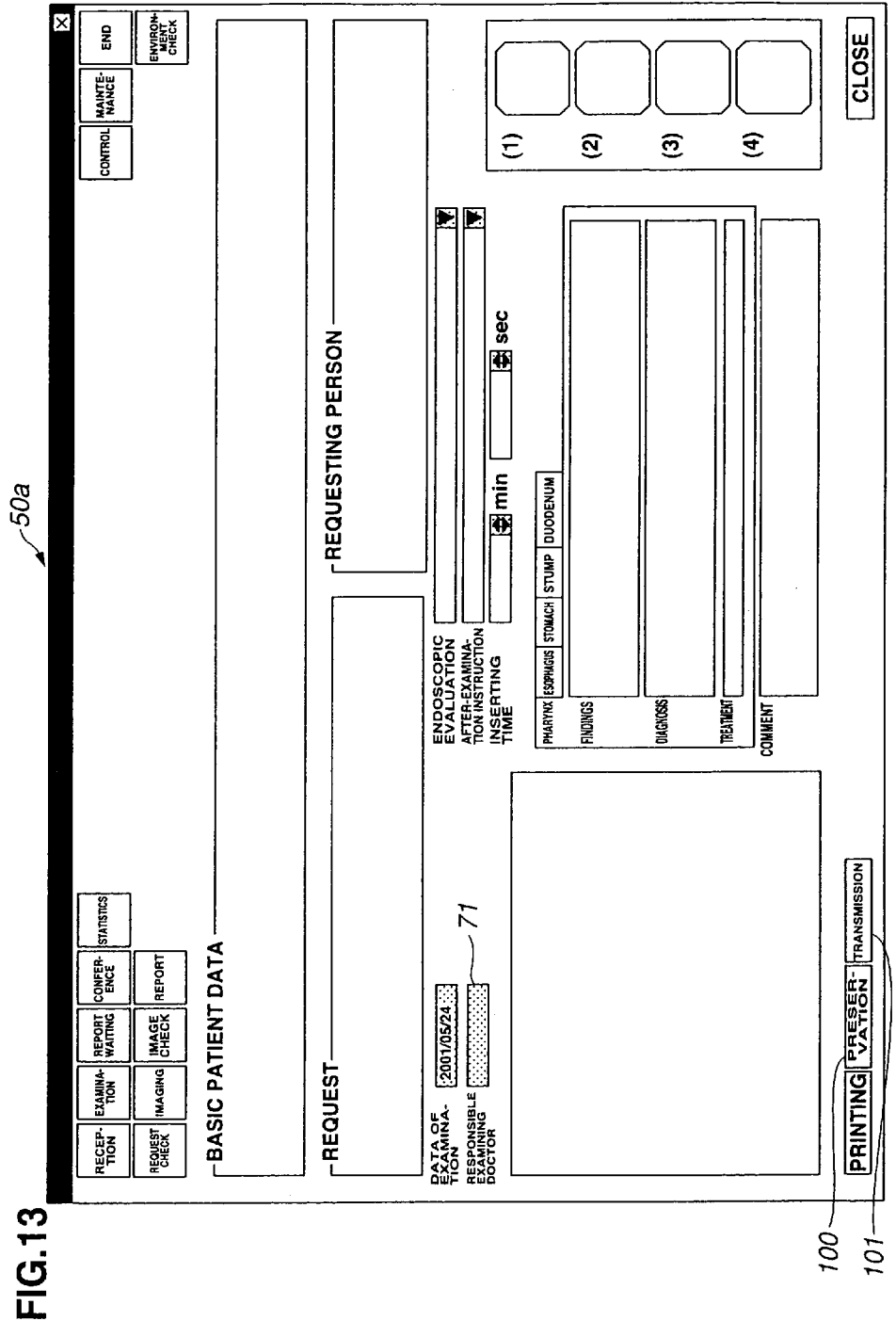

ENDOSCOPIC EXAMINATION SYSTEM WITH SECURITY FOR REPORT PRESERVATION OR TRANSMISSION IMPROVED

The application claims the benefit of Japanese Application No. 2001-228162 filed in Japan on Jul. 27, 2001, the contents of which are incorporated by this reference.

BACKGROUND OF THE INVENTION

1. Field of the Invention

The present invention relates to an endoscopic examination system, or more particularly, to an endoscopic examination system characterized by a login authority or security given by the system.

2. Description of the Related Art

In many conventional endoscopic examination systems, a large number of people share the same terminal. When such an endoscopic examination system is used to edit environmental information describing the details of an environment in which an examination is actually performed or a report describing findings or diagnosis drawn out through an examination, a user's password must be entered without fail at the time of system startup.

However, as far as the conventional system is concerned, even when a doctor or paramedic to whom the authority to edit environmental information or a report is granted logs in, the doctor or paramedic cannot preserve a report or transmit it to a server and a digital clinical recording system. Namely, only a doctor who is in charge of an examination is permitted to preserve or transmit the report because of restrictions for security. Moreover, when a doctor who is in charge of an examination wants to preserve or transmit a report to the server and digital clinical recording system, the doctor must log in the system again. In other words, unless the doctor who is in charge of the examination logs in the system, the report can be neither preserved nor transmitted.

SUMMARY OF THE INVENTION

Accordingly, an object of the present invention is to provide an endoscopic examination system that prompts a user to enter a password at the time of preservation or transmission of a report and controls the preservation or transmission according to a login authority given at that time. The endoscopic examination system does not enable or disable preservation or transmission of a report according to an authority given at the time of logging in the system.

According to the present invention, there is provided an endoscopic examination system consisting mainly of a reporting information input module, a data storage module, a first password discrimination module, and a second password discrimination module. The reporting information input module is used to enter environmental information and reporting information concerning an endoscopic examination. In the data storage module, the environmental information and reporting information entered at the reporting information input module is stored. The first password discrimination module discriminates a first password that enables entry of the environmental information and reporting information at the reporting information input module. The second password discrimination module discriminates a second password entered at the reporting information input module at the time of storage of the reporting information in the data storage module.

Other features of the present invention and the advantages thereof will be apparent from the description below.

BRIEF DESCRIPTION OF THE DRAWINGS

FIG. 1 to FIG. 13 are concerned with an embodiment of the present invention;

FIG. 1 shows the configuration of a medical data file system;

FIG. 2 shows the configuration of an endoscopic examination system included in the medical data file system shown in FIG. 1;

FIG. 3 shows the configuration of a report input/output terminal shown in FIG. 2;

FIG. 4 shows a login acknowledgement screen image that is displayed on the report input/output terminal shown in FIG. 2;

FIG. 5 is a first flowchart describing a processing sequence to be performed by the report input/output terminal shown in FIG. 2;

FIG. 6 shows a screen image that presents a list of patients who are booked for examinations and that is developed according to the first flowchart described in FIG. 5;

FIG. 7 shows a screen image that presents the details of an environment and that is developed according to the first flowchart described in FIG. 5;

FIG. 8 shows a report entry screen image being developed according to the first flowchart described in FIG. 5;

FIG. 9 is a second flowchart describing a processing sequence to be performed by the report input/output terminal shown in FIG. 2;

FIG. 10 shows a screen image that presents the details of an environment and that is developed according to the second flowchart described in FIG. 9;

FIG. 11 shows a first report entry screen image being developed according to the second flowchart described in FIG. 9;

FIG. 12 shows a second report entry screen image being developed according to the second flowchart described in FIG. 9; and FIG. 13 shows a third report entry screen image being developed according to the second flowchart described in FIG. 9.

DETAILED DESCRIPTION OF THE PREFERRED EMBODIMENTS

Figure 1:
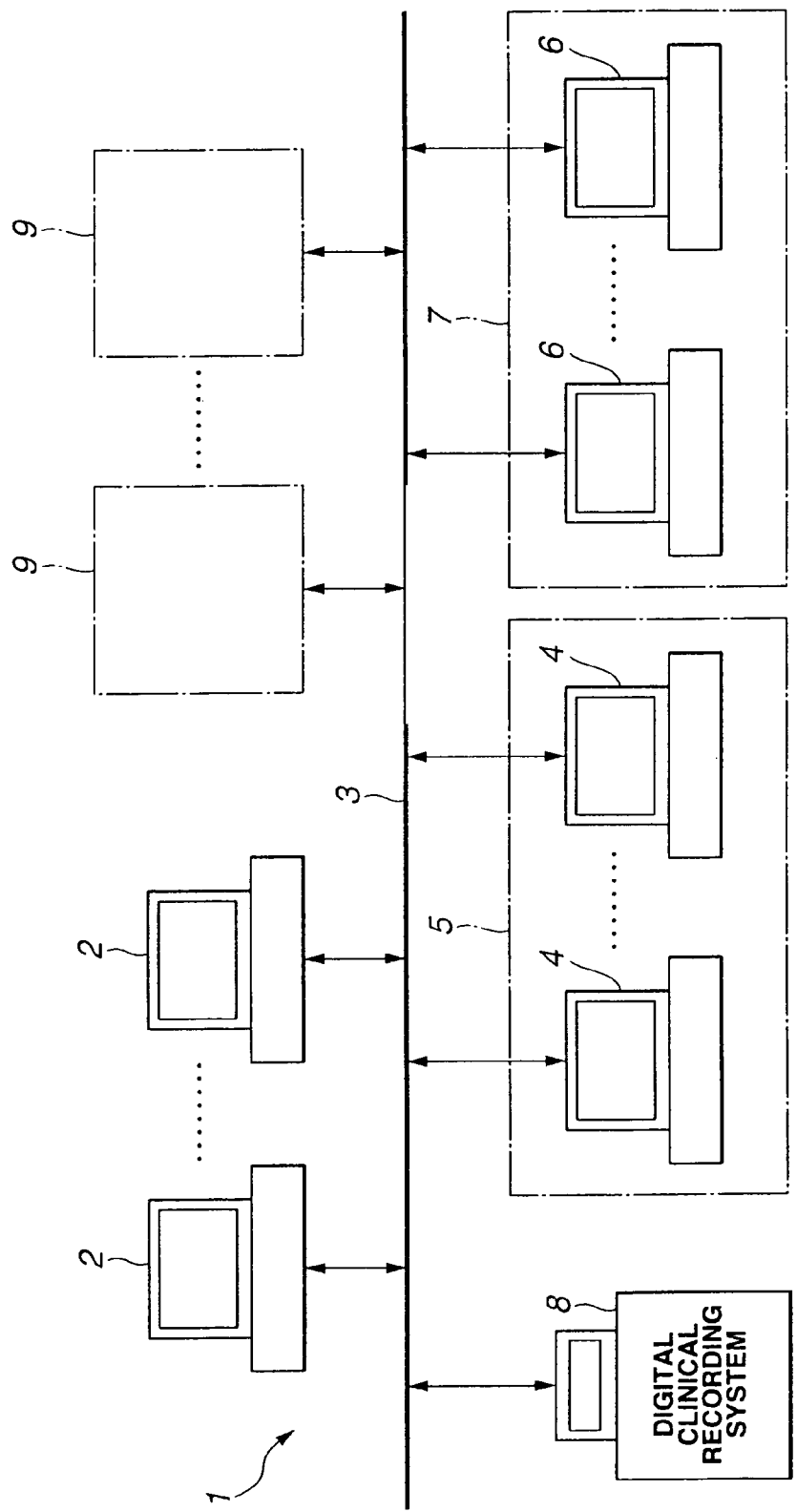

Referring to FIG. 1, a medical data file system 1 in accordance with an embodiment of the present invention consists mainly of a plurality of intra-hospital information terminals 2, an endoscope department 5, a pathology department 7, and a digital clinical recording system 8. The plurality of intra-hospital information terminals 2 is distributed to dispensaries within a hospital. The endoscope department 5 accommodates a plurality of endoscopic examination systems 4 connected to the intra-hospital information terminal 2 over an intra-hospital network 3. The pathology department 7 accommodates a plurality of pathologic examination systems 6 connected on the intra-hospital network 3. The digital clinical recording system 8 that saves in a predetermined format diagnostic data of patients entered at the intra-hospital information terminals 2 or examination data transferred from the endoscope department 5 and pathology department 7 is connected on the intra-hospital network 3. Examination systems 9 accommodated by other departments, such as, ultrasonic examination systems, computed tomography (CT) examination systems, or magnetic resonance imaging (MRI) examination systems can be connected on the intra-hospital network, though they are not illustrated.

Figure 2:
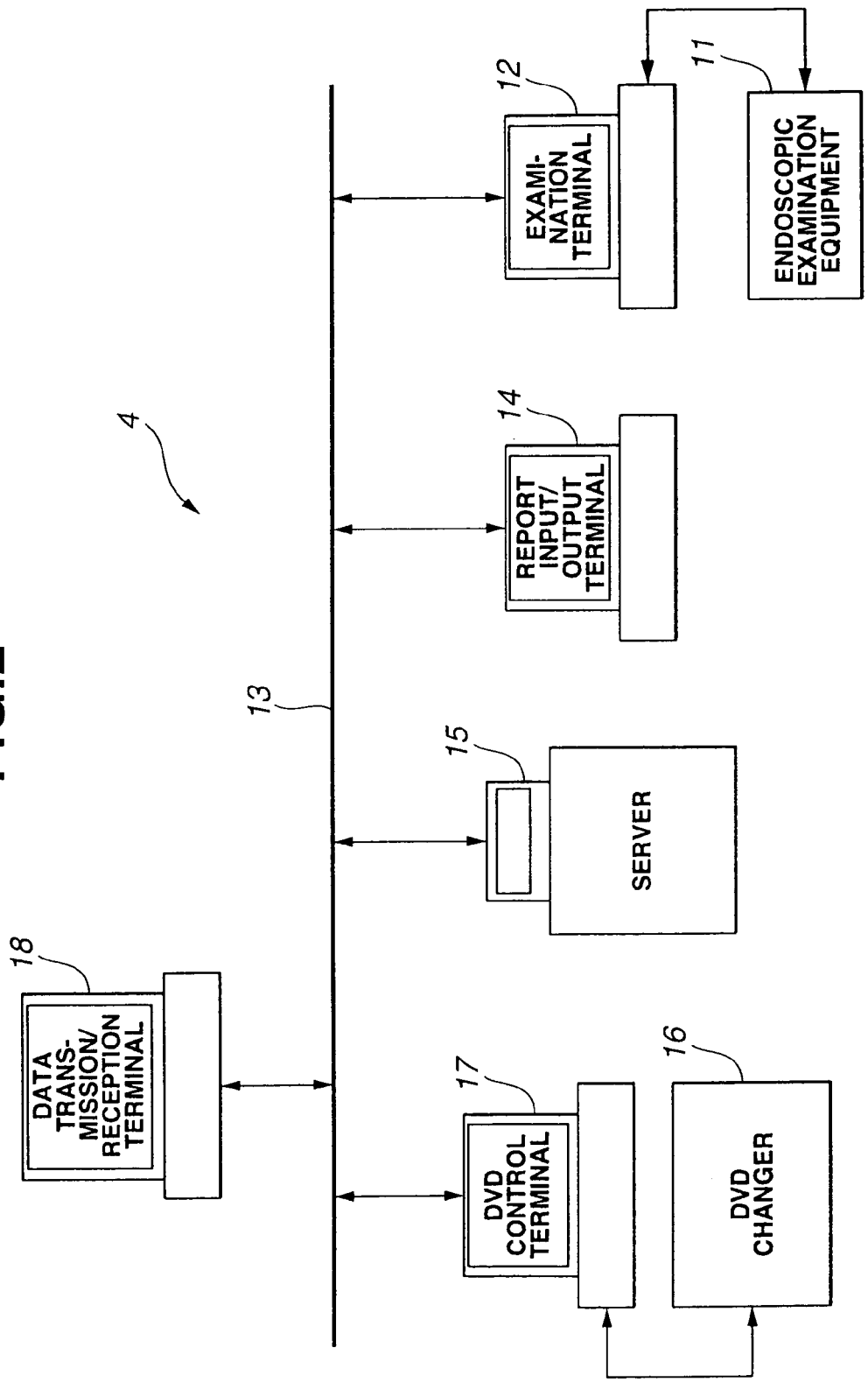

The endoscopic examination system 4 consists mainly of, as shown in FIG. 2, an examination terminal 12, a report input/output terminal 14, a server 15, a digital versatile disk (DVD) control terminal 17, and a data transmission/reception terminal 18. The examination terminal 12 is connected to endoscopic examination equipment 11 that enables examination of an intracavitary region through endoscopic observation. The report input/output terminal 14 is connected to the examination terminal 12 over the system network 13. The report input/output terminal 14 is used to enter environmental information representing the details of an environment (a name of an examining doctor, a name of equipment employed, etc.) under which an endoscopic examination is performed, and reporting information representing the results of an endoscopic examination (findings, diagnosis, etc.), and to produce examination request data for the pathologic examination system 6 based on the reporting information. The server 15 is connected on the system network 13, and preserves examination data (endoscopic image data, etc.) sent from the examination terminal 12, and reporting information and examination request data sent from the report input/output terminal 14. The DVD control terminal 17 is connected on the system network 13, and controls a DVD changer 16 that is a large-capacity recording apparatus used to back up the information preserved in the server 15. The data transmission/reception terminal 18 monitors the digital clinical recording system 8, and controls transfer of examination request data and results-of-examination data.

Incidentally, the pathologic examination system 6 and the examination system 9 accommodated by any other department have the same configuration as the endoscopic examination system 4.

Figure 3:
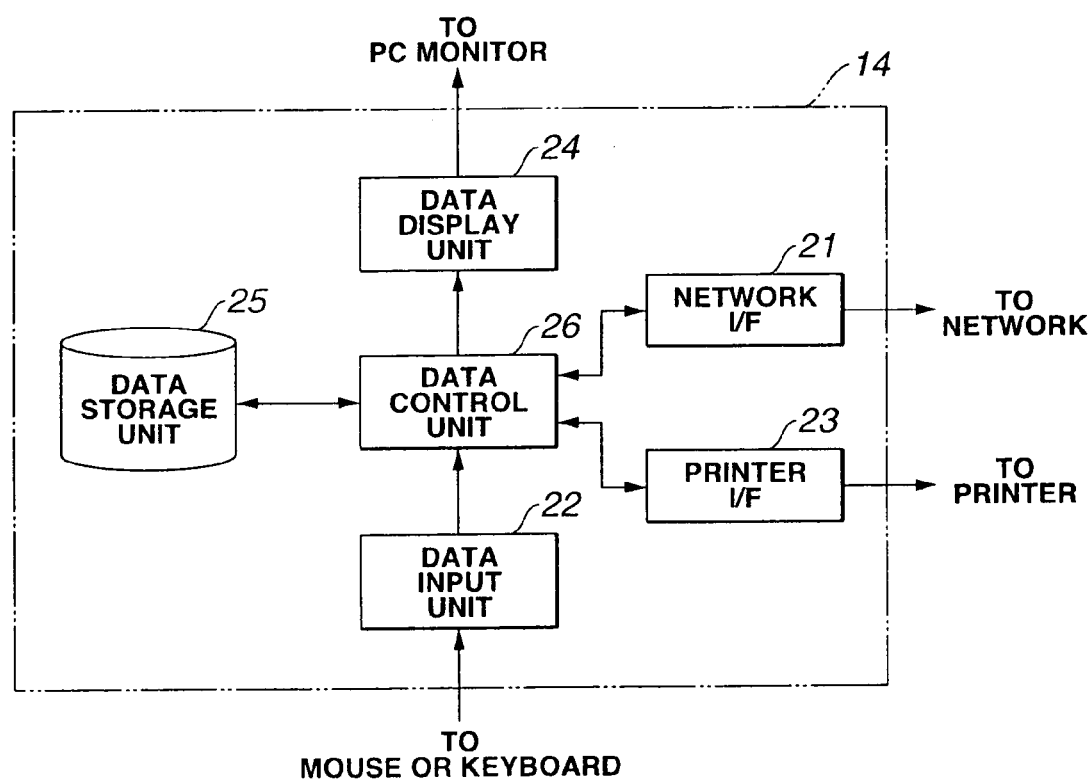

The intra-hospital information terminal 2, examination terminal 12, report input/output terminal 14, DVD control terminal 17, and data transmission/reception terminal 18 are realized with personal computers. As for the components of each of the terminals, for example, the report input/output terminal 14 consists mainly of, as shown in FIG. 3, a network interface 21, a data input unit 22, a printer interface 23, a data display unit 24, and a data control unit 26. The network interface 21 is connected on the system network 13, and data is transferred through the network interface 21. The data input unit 22 is connected to a data input device such as a mouse or keyboard. The printer interface 23 is connected to a data output device such as a printer. The data control unit 26 controls the data input unit 22, printer interface 23, and data display unit 24, performs data processing, and puts the results of processing in the data storage unit 25 such as a hard disk drive.

In the thus-configured medical data file system 1 in accordance with the present embodiment, if endoscopic examination request is issued from the intra-hospital information terminal 2, the data transmission/reception terminal 18 included in the endoscopic examination system 4 receives the endoscopic examination request.

The received endoscopic examination request is registered in a database held in the server 15 by the data transmission/reception terminal 18.

In the endoscopic examination system 4, the endoscopic examination equipment 11 performs an examination according to the endoscopic examination request registered in the server 15.

To be more specific, the examination terminal 12 connected to the endoscopic examination equipment 11 acquires the endoscopic examination request from the server 15. An endoscopic examination is then started.

After the endoscopic examination equipment 11 produces endoscopic images, the examination is terminated. The examination terminal 12 then stores the endoscopic image data in the server 15 in association with the endoscopic examination request.

Once the endoscopic image data is preserved in the server 15, the DVD control terminal 17 copies the endoscopic image data in the server 15 to the DVD changer 16.

At the report input/output terminal 14, environmental information and reporting information concerning an actually performed examination can be entered. The report input/output terminal 14 registers the entered environmental information and reporting information in the database in the server 15 in association with the endoscopic examination request.

The registered environmental information and reporting information will not be deleted from the database in the server 15.

Once the environmental information and reporting information are registered in the server 15, the DVD control terminal 17 copies the environmental information and reporting information held in the server 15 to the DVD changer 16.

Moreover, the report input/output terminal 14 not only registers the environmental information and reporting information in the server 15 but also transmits the reporting information to the digital clinical recording system 8.

Now, a description will be made of production, preservation, and transmission of environmental information and reporting information by the report input/output terminal 14.

Figure 4:
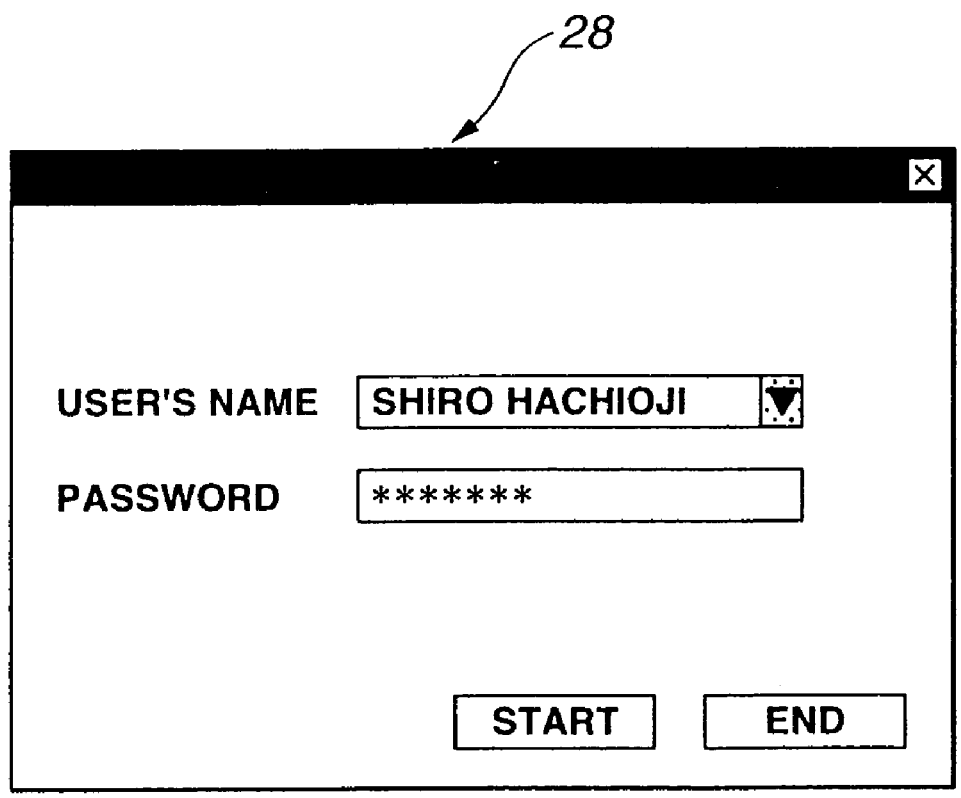

When a software system installed in the report input/output terminal 14 is started up, a login acknowledgement screen image 28 like the one shown in FIG. 4 appears to prompt a user who has started up the system to enter his/her name and password.

Figure 5:
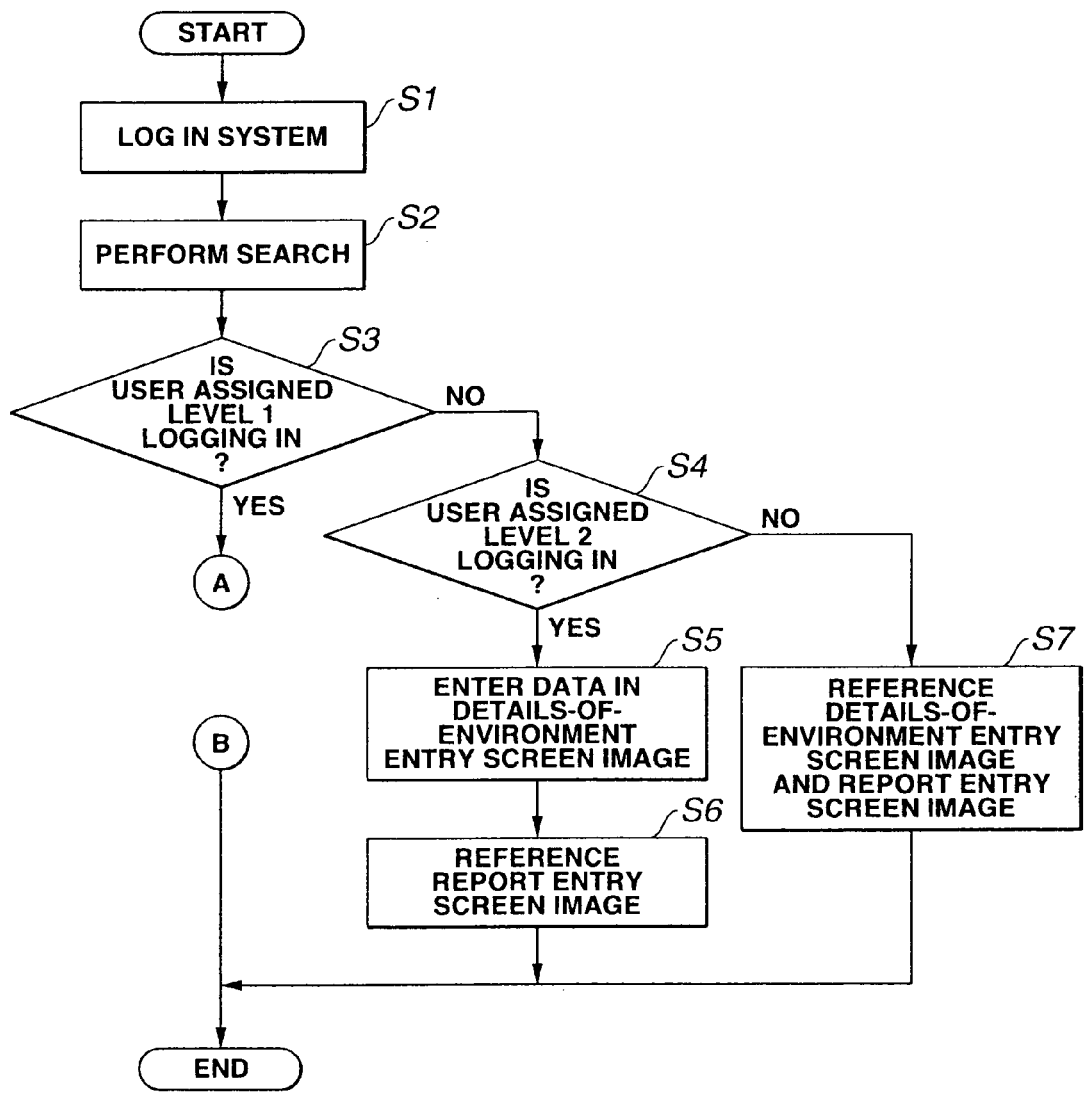
Figure 12:
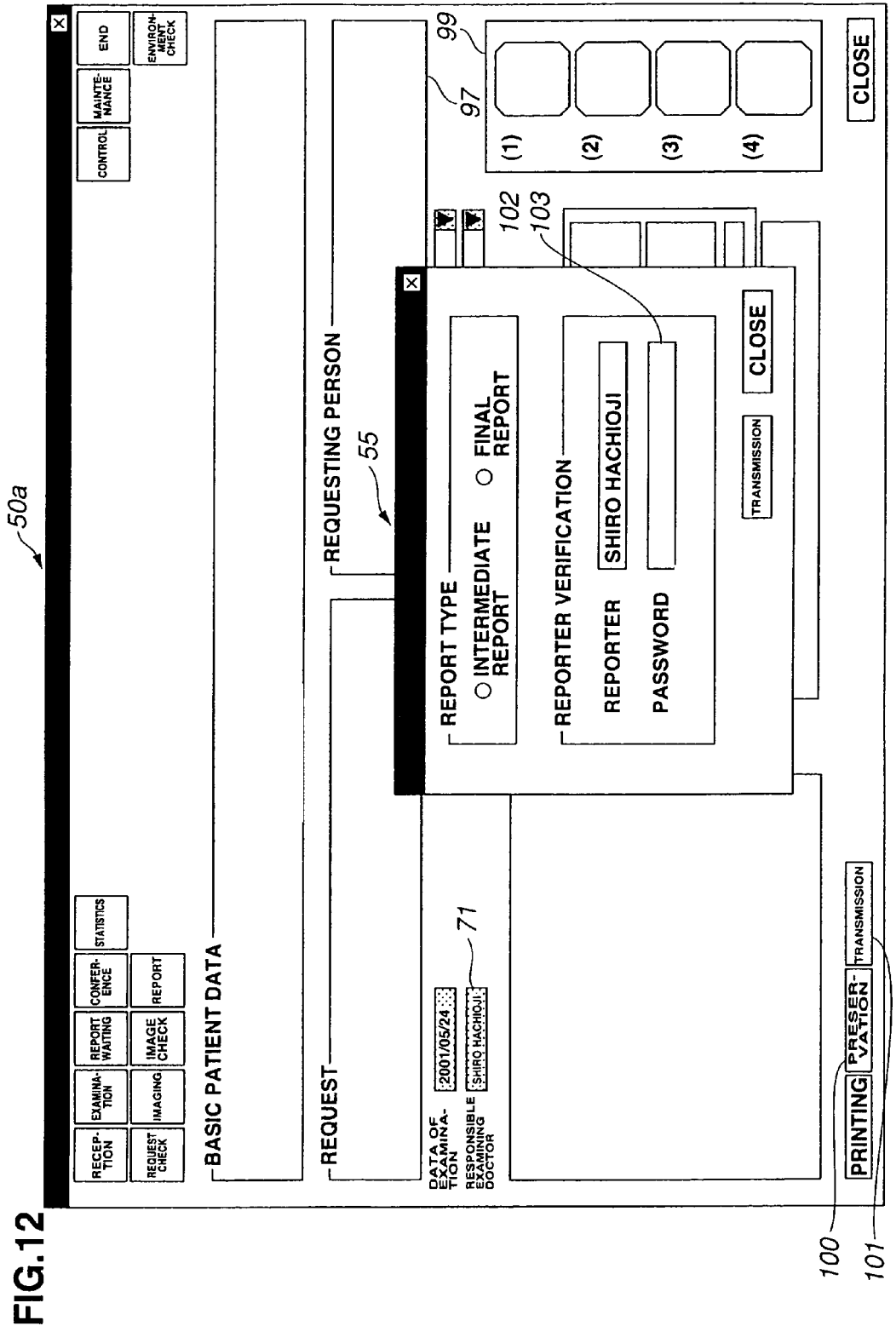

In the login acknowledgement screen image 28, the user's name and password are, as described in FIG. 5, entered in order to log in the system in step S1. A list of patients booked for examinations 29 like the one shown in FIG. 6 then appears. When any examination item for which a patient is booked (not shown) is selected from a list of examinations for which patients are booked 30 within the list of patients booked for examinations 29, the booked examination is allocated to a list of examinations in examining rooms 31. At step S2, an endoscopic examination is performed and completed based on the contents of the list of examinations in examining rooms 31. When the examination is completed, the user's access level at the time of login is judged.

Referring to Table 1, an access level of level 1 is assigned to the main staff who performs an endoscopic examination. An access level of level 2 is assigned to the sub staff who assists in an endoscopic examination. An access level of level 3 is assigned to paramedics other than the main staff and sub staff.

TABLE 1

| Login authority | Entry of environmental information | Entry of reporting information |
| --- | --- | --- |
| Main staff: level 1 | O | O |
| Other staff: level 2 | O | X |
| Other than staff: level 3 | X | X |

As seen from Table 1, the people assigned the access level of level 1 are permitted to enter environmental information and reporting information at the report input/output terminal 14. The people assigned the access level of level 2 are permitted to enter environmental information at the report input/output terminal 14 and view reporting information thereat. The people assigned the access level of level 3 are permitted to view environmental information and reporting information at the report input/output terminal 14.

At step S3, it is judged whether the access level is level 1. If the access level is not level 1, it is judged at step S4 whether the access level is level 2.

If it is judged at step S4 that the access level is level 2. A details-of-environment entry screen image 50 like the one shown in FIG. 7 is displayed at step S5, whereby environmental information can be entered.

TABLE 2

| Login authority | Entry of responsible examining person's name in environmental information entry screen image | User name displayed in password entry window |
|---|---|---|
| Main staff: level 1 | Entered | As long as a password is entered, a responsible examining person (fixed) can preserve or transmit reporting information. But for entry of a password, a responsible examining person can neither preserve nor transmit reporting information. |
|  | Not entered | Not displayed (A user can preserve reporting information alone without a password.) |
| Other staff: level 2 Other than staff: level 3 | Undetermined | Not displayed (Entry of a report is disabled.) |

Figure 8:
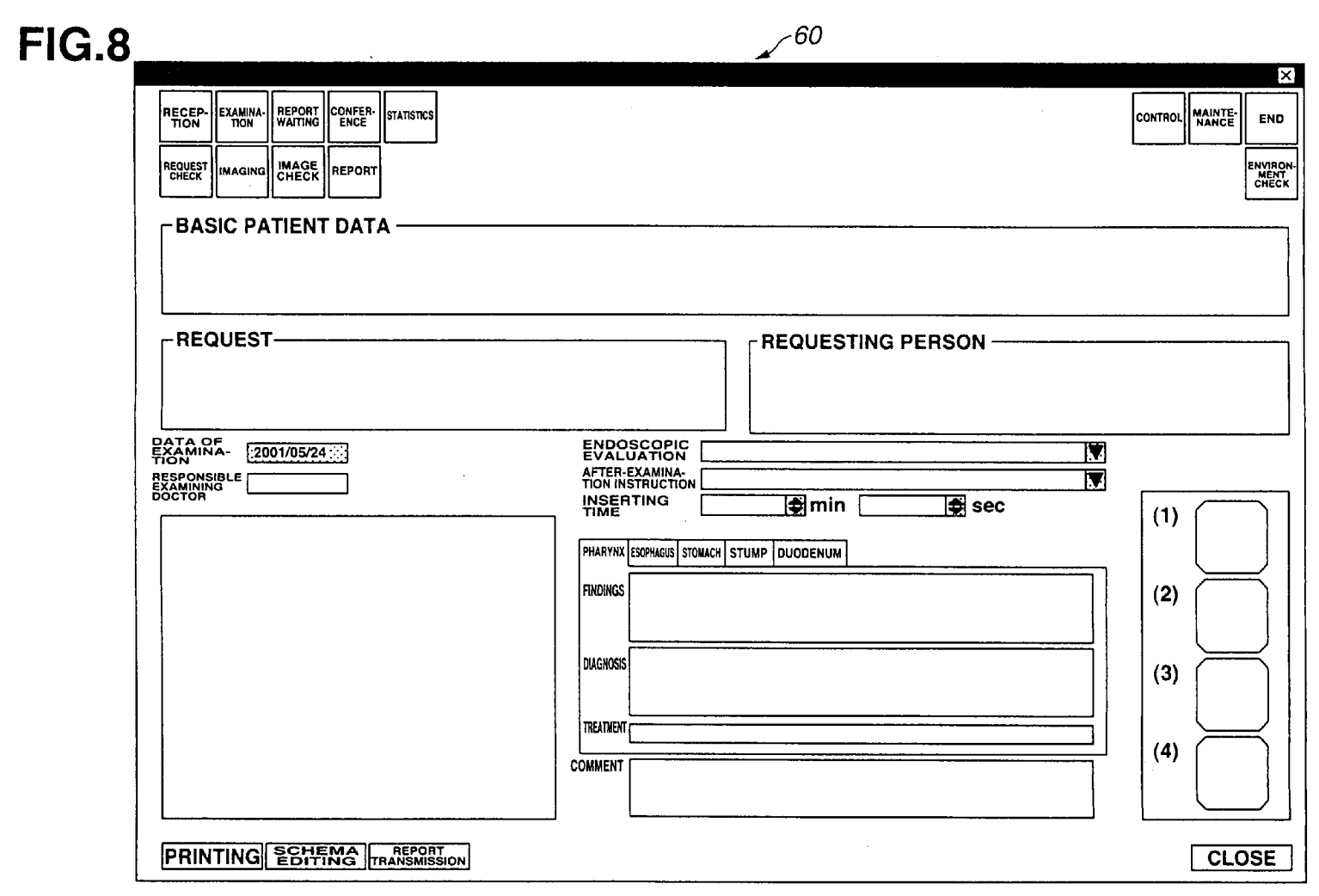

At step S6, the screen image 50 is shifted to a report entry screen image 60 shown in FIG. 8. However, no information can be entered in the report entry screen image 60 but viewing (referencing) alone is enabled. A sequence is then terminated.

If it is judged at step S4 that the access level is not level 2, the details-of-environment entry screen image 50 is merely displayed at step S7 but environmental information cannot be entered in the details-of-environment entry screen image 50. Only viewing the details-of-environment entry screen image 50 and report entry screen image 60 is enabled, and a sequence is terminated.

If it is judged at step S3 in FIG. 5 that the access level is level 1, control is passed to step S31 described in FIG. 9. A details-of-environment entry screen image 50a shown in FIG. 10 appears, whereby environmental information can be entered.

Figure 11:
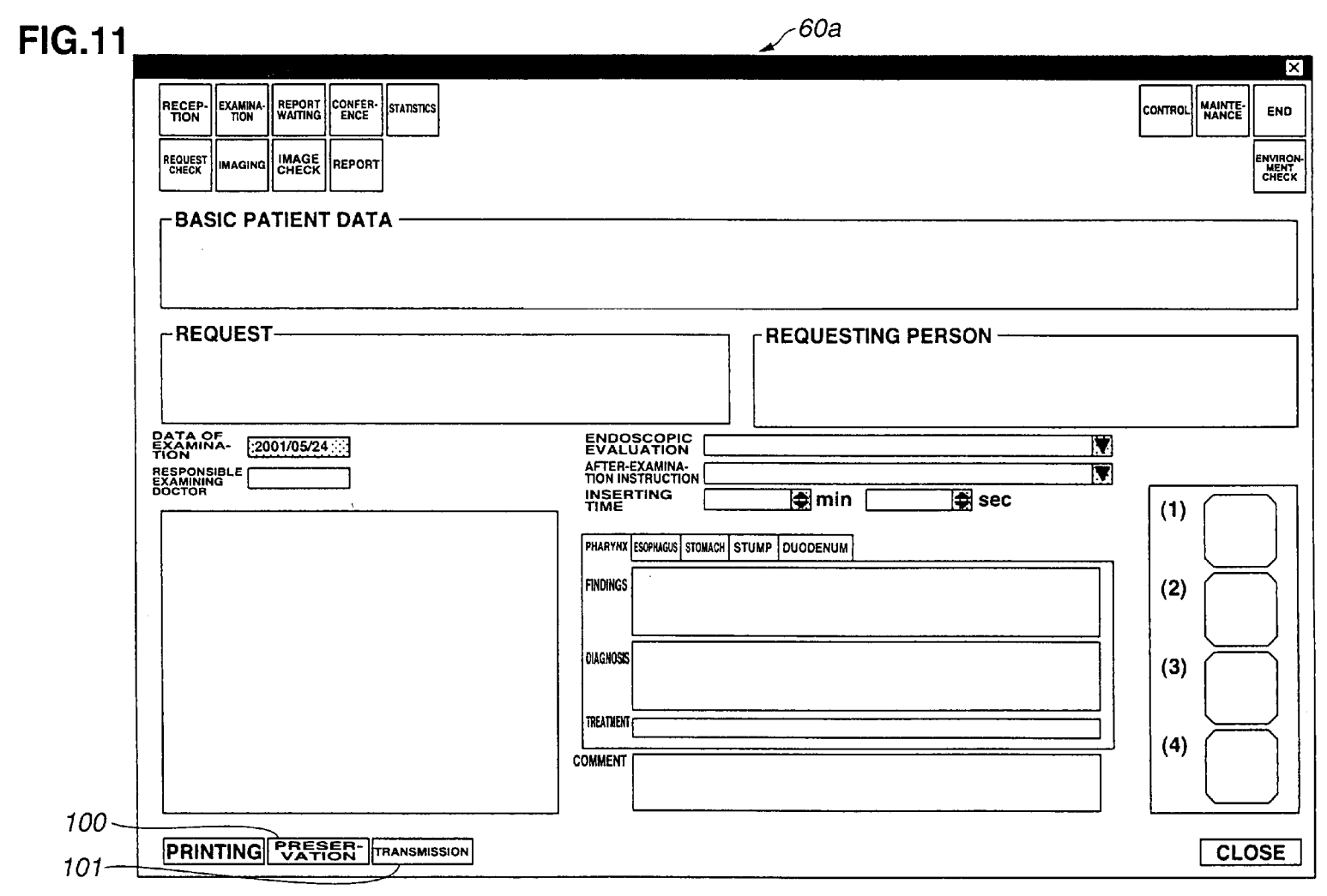

At step S32, the screen image 50a is shifted to a report entry screen 60a shown in FIG. 11. Since the access level is level 1, entry can be made in the report entry screen image 60.

It is judged at step S33 whether a responsible examining doctor's name has been entered in a responsible examining doctor's name entry box 51 in the details-of-environment entry screen image 50a. If it is judged that the responsible examining doctor's name has been entered in the responsible examining doctor's name entry box 51, the responsible examining doctor's name is already entered in a responsible examining doctor's name entry box 71 in the report entry screen image 60a. If a preservation button 100 or a transmission button 101 in the report entry screen image 60a is clicked at step S34, a report transmission window 55 that requests a password for the purpose of checking if a preserving or transmitting person is the responsible examining doctor is displayed on the report entry screen image 60a. At step S35, it is judged whether a password entered in the report transmission window 55 is the responsible examining doctor's password. If the entered password is the responsible examining doctor's password, data entered in the report entry screen image 60 is preserved in the server 15 at step S36. Otherwise, the data entered in the report entry screen image 60 is transmitted to the digital clinical recording system 8. The sequence described in FIG. 5 is then terminated (in case of transmission, when the data entered in the report entry screen image 60 is transmitted to the digital clinical recording system 8, the data is preserved in the server 15 at the same time).

At step S33, a responsible examining doctor's name may not be entered in the responsible examining doctor's name entry box 51 but a Pending button 52 in the details-of-environment entry screen image 50a may be clicked. In this case, as shown in FIG. 13, the responsible examining doctor's name entry box 71 in the report entry screen image 60b is left blank. The preservation button 100 is validated. If the preservation button 100 is clicked, data entered in the report entry screen image 60 is preserved in the server 15 at step S37. The sequence described in FIG. 5 is then terminated.

As mentioned above, according to the present embodiment, preservation or transmission of a report is not enabled or disabled based on an authority given at the time of logging in a system. Entry of a password is requested at the time of preservation or transmission of a report, and the preservation or transmission is controlled based on a login authority given at that time.

According to the present invention, it is apparent that a wide range of different embodiments can be constructed based on the invention without a departure from the spirit or scope of the invention. The present invention will be limited to the appended claims but not restricted to any specific embodiment.

What is claimed is:

1. An endoscopic examination system comprising:
    a reporting information input module for use in entering environmental information and reporting information concerning an endoscopic examination;
    an endoscopic examination control module communicating with the input module, the endoscopic examination control module providing data for and controlling the endoscopic examination;
    a data storage module in which the environmental information and reporting information entered at the reporting information input module are stored;
    a first password discrimination module for discriminating a first password that enables entry of the environmental information and reporting information at said reporting information input module; and
    a second password discrimination module for discriminating a second password entered at said reporting information input module, wherein said second password discrimination module is adapted to discriminate the second password which is only used for initiating storage of the reporting information and which is compared with a discrimination content of the first password discriminated by the first password discrimination module at the time of storage of the reporting information in said data storage module when the first password discrimination module has discriminated the first password and enabled entry of the environmental information and reporting information at said reporting information input module.

2. An endoscopic examination system according to claim 1, wherein said first password is associated with any of a plurality of access levels that defines access authorities permitting a user to access said data storage module.

3. An endoscopic examination system according to claim 2, wherein said plurality of access levels defining access authorities includes at least:
   a first level permitting said user to store both the environmental information and reporting information in said data storage module and to view both the environmental information and reporting information;
   a second level permitting said user or another user to store both the environmental information and reporting information in said data storage module and to view the reporting information alone; and
   a third level permitting said user or another user to merely view both the environmental information and reporting information stored in said data storage module.

4. An endoscopic examination system according to claim 3, wherein only when said first password is associated with said first level said second password discrimination module requests entry of said second password at said reporting information input module, and discriminates said second password only for initiating storage of the reporting information.

5. An endoscopic examination system according to claim 1, further comprising an information transmission module for transmitting the environmental information and reporting information over a network outside said system, wherein:
   said information transmission module controls transmission of the environmental information and reporting information over said network according to the second password discriminated by said second password discrimination.

6. An endoscopic examination system according to claim 5, wherein the first password is associated with any of a plurality of access levels that defines access authorities permitting a user to access said data storage module.

7. An endoscopic examination system according to claim 6, wherein the plurality of access levels defining access authorities includes at least:
   a first level permitting said user to store both the environmental information and reporting information in said data storage module and to view both the environmental information and reporting information;
   a second level permitting said user or another user to store both the environmental information and reporting information in said data storage module and to view the reporting information alone; and
   a third level permitting said user or another user to merely view both the environmental information and reporting information stored in said data storage module.

8. An endoscopic examination system according to claim 7, wherein only when the first password is associated with the first level, said second password discrimination module requests entry of the second password at said reporting information input module, and discriminates the second password.

9. An endoscopic examination system according to claim 8, wherein only when the first password is associated with the first level, said information transmission module requests entry of the second password at said reporting information input module, and enables transmission of the environmental information and reporting information over said network.

10. An endoscopic examination method comprising:
    a reporting information input step of entering environmental information and reporting information concerning an endoscopic examination at a reporting information input module;
    an examination information and control step of providing data for and controlling the endoscopic examination using the environmental and reporting information from the input step, at an endoscopic examination control module;
    a data storage step of storing the environmental information and reporting information, which are entered at said reporting information input module, in a data storage module;
    a first password discrimination step of discriminating a first password that enables entry of the environmental information and reporting information at said reporting information input module; and
    a second password discrimination step of discriminating a second password entered at said reporting information input module at said data storage step of storing the reporting information when the first password discrimination module has discriminated the first password and enabled entry of the environmental information and reporting information at said reporting information input module, and the second password discrimination step only used for initiating storage of the reporting information and which is compared with a discrimination content of the first password discriminated by the first password discrimination module.

11. An endoscopic examination system according to claim 10, wherein said first password is associated with any of a plurality of access levels that defines access authorities permitting a user to access said data storage module.

12. An endoscopic examination method according to claim 11, wherein the plurality of access levels defining access authorities includes at least:
    a first level permitting said user to store both the environmental information and reporting information in said data storage module and to view both the environmental information and reporting information;
    a second level permitting a said user or another user to store both the environmental information and reporting information in said data storage module and to view the reporting information alone; and
    a third level permitting said user or another user to merely view both the environmental information and reporting information stored in said data storage module.

13. An endoscopic examination method according to claim 12, wherein at said second password discrimination step, only when the first password is associated with the first level, entry of the second password at said reporting information input module is requested and the second password is discriminated.

14. An endoscopic examination method according to claim 10, further comprising an information transmission step of transmitting the environmental information and reporting information over a network outside said system, wherein:
    at said information transmission step, transmission of the environmental information and reporting information over said network is controlled based on the second password discriminated at said second password discrimination step.

15. An endoscopic examination method according to claim 14, wherein the first password is associated with a plurality of access levels that defines access authorities permitting a user to access said data storage module.

16. An endoscopic examination method according to claim 15, wherein the plurality of access levels defining access authorities includes at least:
- a first level permitting said user to store both the environmental information and reporting information in said data storage module and to view both the environmental information and reporting information;
- a second level permitting said user or another user to store both the environmental information and reporting information in said data storage module and to view the reporting information alone;
- a third level permitting said user or another user to merely view both the environmental information and reporting information stored in said data storage module.

17. An endoscopic examination method according to claim 16, wherein at said second password discrimination step, only when the first password is associated with the first level, entry of the second password at said reporting information input module is requested and the second password is discriminated.

18. An endoscopic examination method according to claim 17, wherein at said information transmission step, only when the first password is associated with the first level, entry of the second password at said reporting information input module is requested, and transmission of the environmental information and reporting information over said network is enabled.

19. An endoscopic examination system according to claim 1, wherein said first password is associated with any of a plurality of access levels that define access authorities permitting a user to access said data storage module, and said second password discrimination module requests entry of said second password from said user or another user with a required access level only for reporting information at said reporting information input module, and discriminates said second password.

20. An endoscopic examination system according to claim 3, wherein reporting information at said reporting information input module only when said first password is associated with said first level from said user, and said second password discrimination module requests entry of said second password from said user only for reporting information at said reporting information input module, and discriminates said second password.

* * * * *

UNITED STATES PATENT AND TRADEMARK OFFICE
CERTIFICATE OF CORRECTION

PATENT NO.         : 7,457,963 B2  
APPLICATION NO. : 10/202140  
DATED                 : November 25, 2008  
INVENTOR(S)       : Nobuyasu Ito et al.

Page 1 of 1

It is certified that error appears in the above-identified patent and that said Letters Patent is hereby corrected as shown below:

<u>Column 8, Claim 11, Line 31:</u>

"An endoscopic examination system"

should read

-- An endoscopic examination method --

Signed and Sealed this

Third Day of March, 2009

JOHN DOLL  
*Acting Director of the United States Patent and Trademark Office*